United States Patent [19]

Clark et al.

[11] 4,109,505
[45] Aug. 29, 1978

[54] AUTOMATED BLOOD ANALYSIS SYSTEM

[75] Inventors: Justin S. Clark; Lloyd George Veasy, both of Salt Lake City, Utah

[73] Assignee: Primary Children's Hospital, Salt Lake City, Utah

[21] Appl. No.: 566,023

[22] Filed: Apr. 7, 1975

Related U.S. Application Data

[62] Division of Ser. No. 490,603, Jul. 22, 1974, Pat. No. 3,910,256, which is a division of Ser. No. 319,561, Dec. 29, 1972, Pat. No. 3,838,682.

[51] Int. Cl.² .................................................. G01N 27/26
[52] U.S. Cl. ..................................... 73/1 R; 204/195 B
[58] Field of Search ............... 324/30 R; 73/1 R, 1 G; 204/195 B, 195 P

[56] References Cited
U.S. PATENT DOCUMENTS

| | | | |
|---|---|---|---|
| 3,055,220 | 9/1962 | Ryan et al. | 73/446 |
| 3,263,554 | 8/1966 | Pickels | 73/425.6 |
| 3,648,159 | 3/1972 | Stansell et al. | 324/30 R |
| 3,658,478 | 4/1972 | Spergel | 324/30 R |
| 3,661,748 | 5/1972 | Blackmer | 204/195 P |
| 3,874,850 | 4/1975 | Sorensen et al. | 324/30 R |
| 3,884,640 | 5/1975 | Lock et al. | 324/30 |

*Primary Examiner*—S. Clement Swisher
*Attorney, Agent, or Firm*—Lynn G. Foster

[57] ABSTRACT

A system for automatically withdrawing blood from a patient and testing various parameters of the blood, such as oxygen saturation, hemoglobin, gas content ($PO_2$, $PCO_2$) and pH, includes a withdrawal unit which automatically withdraws a measured volume of blood, and returns all of it to the patient except a small measured quantity which is provided to an analysis unit that measures the gas content and pH. The withdrawal unit includes provision for continuously monitoring patients' blood pressure, irrigation from a standard I.V. source between blood withdrawals, or a constant low flush of saline, alternatively, as well as detection of any air in the blood, which results in shutting down the system and activating an air alarm. The withdrawal unit also has provision for automatically withdrawing a small sample of blood, measuring oxygen content, and returning all blood to the patient, all on a programmed basis. The analysis unit includes two-point gas and pH calibration and includes use of calibration fluid for washout. In each complete use cycle, blood from the withdrawal unit is washed into the analysis unit and blood in the analysis unit is moved and washed out using saline, water and calibration fluids. The withdrawal unit may be used alone to acquire blood samples, and the analysis unit may be fed by more than one withdrawal unit or by manually-acquired blood specimens.

9 Claims, 6 Drawing Figures

(ANALYSIS UNIT)

FIG. 1 (SYSTEM)

FIG. 2 (WITHDRAWAL UNIT)

FIG. 3 (ANALYSIS UNIT)

FIG. 4 (TIMING UNIT)

FIG. 6

AUTOMATED BLOOD ANALYSIS SYSTEM

The invention described herein was made in the course of work under a grant or award from the Department of Health, Education, and Welfare.

CONTINUITY

This application is a division of our copending U.S. Patent application Ser. No. 490,603, filed July 22, 1974, now U.S. Pat. No. 3,910,256, issued Oct. 7, 1975, which is a division of our Patent application Ser. No. 319,561, filed Dec. 29, 1972, now U.S. Pat. No. 3,838,682, issued Oct. 1, 1974.

BACKGROUND

1. Field of Invention

This invention relates to automated blood analysis systems, and more particularly to apparatus for automatically withdrawing and testing blood.

2. Prior Art

The proper management of patients who are critically ill with respiratory or cardiovascular disorders requires frequent monitoring of various blood parameters such as oxgygen saturation, gas content and pH. While adequate oxygenation is necessary for maintenance of life, it is also important to avoid excessively high arterial $PO_2$, particularly in new born infants, in order to prevent Retrolental Fibroplasia and possible central nervous system damage. Similarly, the duration of high oxygen concentrations must be kept to a minimum in infants to prevent possible toxic effects in the lungs. There are numerous other situations, such as in diagnosis of critical illness, monitoring a patient's condition during certain corrective procedures, and in intensive care programs wherein blood parameters must be frequently analyzed.

However, frequent manual withdrawal of blood is undesirable due to the increased opportunity for the entrance of air emboli in the blood stream, and to the attendant necessary morbidity, particularly in new born infants. Similarly, multiple usage of an indwelling catheter has heretofore nonetheless required rearrangement of external tubing to adjust between blood withdrawal and irrigation configurations, which is subject to human error and which also presents increased incidence of air emboli infusion. Some systems known to the prior art require a constant flow of blood therethrough which unnecessarily increases blood contact with foreign surfaces, which can increase the opportunity for contamination of the blood, or which may damage the blood. On the other hand, systems known to the art which discharge withdrawn blood to waste after testing thereof have utilized an excessive amount of blood which becomes particularly intolerable in the case of critically ill new born and pre-mature infants. Other systems subject the patient to a risk of electric shock due to a continuous contact existing between the patient and electric potentials within the blood testing equipment or sensors. Systems which return blood to the patient cannot be used for destructive tests (such as glucose analysis, flame photometry, etc.).

As is known, it is common to employ saline as a compatible vehicle for use in blood pumps and tubing systems of blood test units since some of its chemical properties approach that of blood. However, depending upon the characteristics of the individual patient, blood equipment and use, it is possible to infuse undue amounts of saline into the patient's blood stream, thereby resulting in a dangerous sodium buildup. Use of intravenous solutions (I.V.) which are desirable to the patient for its nutritive or other value, as a vehicle in blood systems avoids the sodium buildup problem, but, on the other hand, has a tendency to contaminate the system with respect to the blood test transducers which are used.

Some blood parameters differ markedly from saline and pure water, which are used for cleaning a system, and may concurrently require a test principle which includes a very slow process, such as diffusion across a membrane. Repetitive usage of an effective blood analysis system requires automated washout between samples. On the other hand, efficient usage of such a system, particularly with multiple blood sources, dictates that a rather rapid analysis cycle be achievable. Blood analysis units known to the art require both manual cleaning and manual calibrations between samples.

In addition, systems known to the art do not provide adequate tests for membrane leakage in gas detection tests.

OBJECTS AND BRIEF SUMMARY OF THE INVENTION

A principal object of the present invention is to provide improved blood analysis capability.

Another object of the invention is to provide improved automatic blood withdrawal and analysis units.

A further object of the invention is provision of a blood withdrawal unit capable of automatic interspersion of blood withdrawal cycles with constant irrigation or flush cycles for use with a continuously indwelling catheter.

Still other objects of the invention include provision of blood apparatus with improved self cleaning, automatic calibration, shorter equilibration times, and with improved integrity of the test results.

Further objects of the invention include an automated blood analysis system which requires very little blood, isolates hazardous blood testing units from the patient, is self-calibrating and self cleaning, and is capable of utilization with multiple automatically or manually derived blood specimens.

Other important objects are the provision of an automatic blood testing system having: a novel fluid reservoir; capability to return substantially all withdrawn blood to the patient; an analyzer which can be shifted between and used with any one of several blood withdrawal units; an analyzer/withdrawal arrangement where only the withdrawal unit requires sterilization and contamination of the withdrawal unit by the analyzer is precluded; a combination blood withdrawal/infusion unit where intravascular (I.V.) solution flow is continuous, i.e. to the patient during the infusion mode and to waste during blood withdrawal; initial calibration fluids which are used to displace blood within the blood testing system; a control arrangement based on sensing a blood/transparent fluid interface which moves within the system according to a program.

According to the present invention, an automated blood system adapted for connection with an indwelling catheter includes alternatively operable means for providing I.V. infusion, constant catheter flush, or blood withdrawal, without necessitating rearrangement of apparatus, by means of a novel and improved automated valving arrangement.

In accordance with the present invention, automatic blood analysis apparatus is provided with a plurality of sources of fluid, said fluid having a characteristic similar to a characteristic of blood which is to be tested, said apparatus including testing stations interconnected with said fluid sources by valve means programmed in a fashion to provide calibration of said test station prior to the testing of blood therewith and further calibration following the testing of blood therewith. In further accord with the present invention, automated blood testing apparatus includes a gas test station and a pH test station, and valving means for applying blood first to said pH test station and then to both said pH test station and said gas test station, the fluid in said test stations being in electrical communication with one another, said apparatus providing a first test of blood at said pH test station at said first time and a second test at said pH station at said second time, a substantial variation in the results of said first and second tests being indicative of a fault at said gas test station. In still further accord with the present invention, washout water used to cleanse a test station is provided with a measure of a substance for which blood is to be tested, thereby to provide the presence of said substance in an amount on the same order of magnitude of the concentration of said substance normally found in a test therefor, whereby to reduce the equilibration time required to perform a test for said substance. In accordance still further with the present invention, improved programming and arrangement of valve means enhances the drawing of blood into test stations, and the cyclic cleaning of a plurality of test stations with various fluids.

The present invention provides automatic blood withdrawal and/or automatic blood testing with great safety and at a relatively high rate of speed. Blood/Transparent fluid interface is minimized by a novel reservoir and the interface serves to control the operation of the system. Blood withdrawal apparatus in accordance herewith is capable of withdrawing precise amounts of blood, for use in the automated analysis operations or otherwise, in between the regulated infusion of catheter flushing solution or intravenous irrigation solution. The invention permits rapid cyclic testing of different blood specimens, with automatic washout between tests, and automatic and efficient calibration. The invention eliminates the need for multiple catheters or reconfigurations of withdrawal systems in order to achieve steady state monitoring and infusion in conjunction with periodic blood withdrawal. Blood withdrawal may be achieved utilizing solutions which are compatible with blood testing, or utilizing intravenous irrigation solutions which avoid a buildup of excessive concentrations of undesirable compounds in the blood. The automated testing of blood is achieved in accordance with the invention in a manner utilizing extremely small amounts of blood and returning substantially all withdrawn blood to the patient. Minute amounts of blood used for certain tests are exhausted to waste, thereby avoiding any risk of cross contamination and blood damage problems. Testing of blood from a plurality of automatic or manually withdrawn specimens in a relatively short period of time is readily achieved, due not only to the complete autonomy of the automated withdrawal and testing units, but well as to fast and efficient washout and calibration procedures. One analysis unit can service several withdrawal units. Need for sterilization of the analyzer is obviated and cross contamination, analyzer-to-withdrawal unit, is avoided. The withdrawal unit may be constructed to both infuse I.V. fluid and withdrawal blood, with I.V. fluid being exhausted to waste during the withdrawal mode. Preferably, calibration fluids drive the blood within the system.

Other objects, features and advantages of the present invention will become more apparent in light of the following detailed description of a preferred embodiment thereof, as illustrated in the accompanying drawings.

DESCRIPTION OF PREFERRED EMBODIMENT

Figure 1:
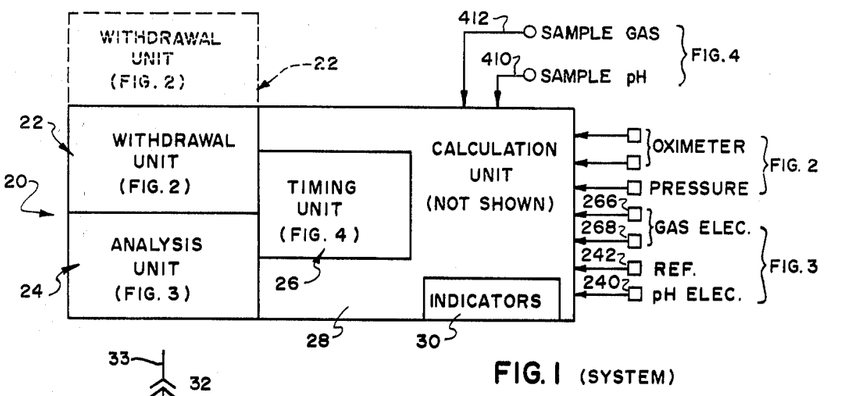
FIG. 1 is a simplified block diagram of a system in which the present invention may be incorporated.

Referring now to FIG. 1, a blood analysis system 20 which may incorporate the precepts of the present invention includes one or more withdrawal units 22, an analysis unit 24 and a timing unit 26, which may be included within a calculation unit 28 (not shown) if desired, or may be provided separately as shown herein. Even though more than one withdrawal unit may be used, on a consecutive basis, to deliver blood to the analysis unit, physical isolation, as explained more thoroughly hereinafter, avoids cross contamination. The calculation unit 28 may include indicators 30 if desired, or these may be provided separately, such as at an intensive care unit nurses' station or other remote location. The calculation unit 28 may, if desired, comprise a blood analysis calculation unit of any type heretofore known in the art, there being a plethora of such units available in the marketplace for "bench" testing of blood samples. On the other hand, the calculation unit 28 may comprise a computing system, such as a large scale computer which may be time shared with other functions, or a minicomputer dedicated to operation with a withdrawal unit 22 and an analysis unit 24 of the type disclosed herein. In the event that the calculation unit includes a multi-function computer of some sort, the timing functions may be readily provided thereby, rather than by a discrete timing unit 26 of the type described with respect to FIG. 4 hereinafter. It should be understood that the apparatus which provides the timing and calculation of test results is not germane to the present invention; instead, the present invention is concerned with the improvements in the withdrawal unit 22 as described with respect to FIG. 2 hereinafter and in the analysis unit 24 as described with respect to FIG. 3 hereinafter, and with the timing of functions performed thereby so as to achieve new and improved operational functions and results.

Figure 2:
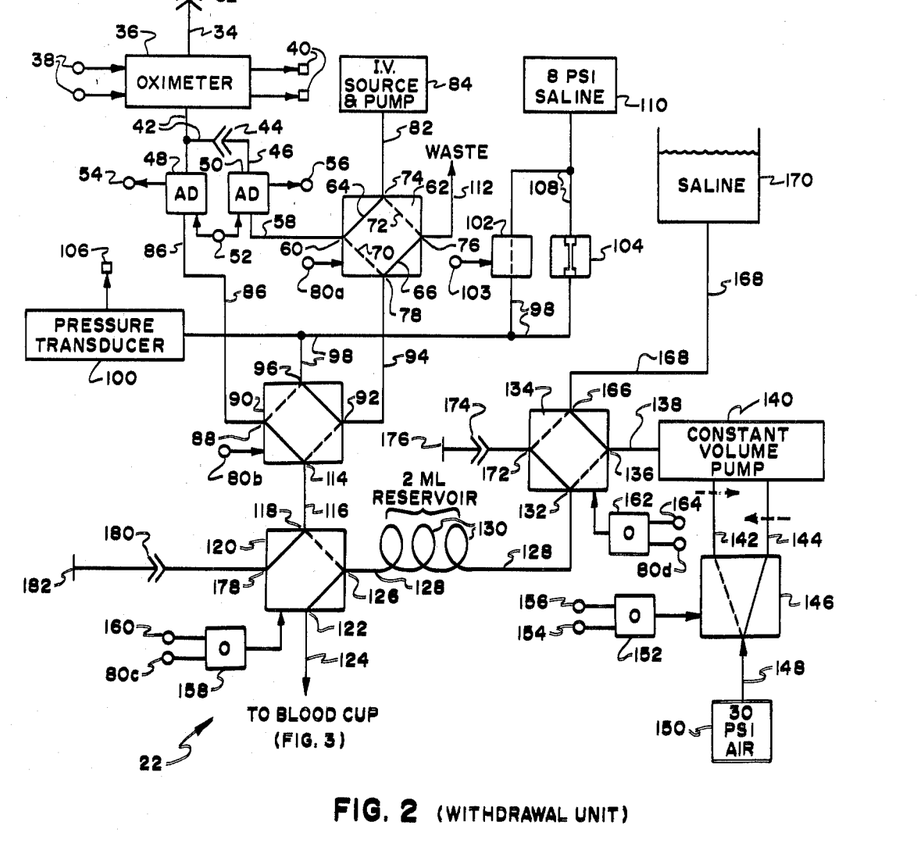
FIG. 2 is a schematic block diagram of an automated blood withdrawal unit in accordance with the present invention.

Referring now to FIG. 2, a fitting 32, which may be of the well known Luer type of fitting, is adapted for connection with a suitable arterial, venous, or umbilical catheter 33 of any type known for use in fluid communication with the blood system of the patient. The fitting 32 is connected by tubing 34 to an oximeter 36 which is provided with electrical inlet connections 38 and electrical output connections 40. The tubing 34 must be essentially impervious to diffusion of gas to prevent or minimize $O_2$ and $CO_2$ losses. KEL-F and nylon tubing have proved satisfactory. The oximeter 36 may be of any well known type which typically measures oxygen saturation. The oximeter 36 is calibrated with saline in the tubes of the withdrawal unit which remains there and is used as the medium for displacing blood within the withdrawal unit. The appearance of a stable blood/saline interface at the oximeter terminates withdrawal thereby minimizing the amount of blood removed. The blood is returned to the patient, as hereinafter more fully explained. This procedure allows more frequent examination of blood. If a stable blood/saline interface does not appear at the oximeter during withdrawal after a predetermined time, withdrawal ceases as constant volume pump 140 only cycles once.

The oximeter 36 is connected by tubing 42 to a fitting 44 and by means of additional tubing 46 to a pair of air detectors (AD) 48, 50. The air detectors 48, 50 include an electric signal input 52 and respective signal outputs 54, 56. It is to be noted that the air detector output terminals 54, 56 are depicted in a circular configuration in contrast with the square configuration of the oximeter output terminals 40. This is to distinguish between electrical signals which are used directly in the control of the system of the present invention (such as signals at the terminals 54, 56) which are depicted in round configuration, from output signals which are used externally of the system so as to derive information relating to blood which is being tested (such as signals at the terminals 40) which are depicted in the square configuration. The air detector 50 is connected by tubing 58 to a port 60 of a fluid valve 62 which, along with similar other valves herein, is depicted schematically as a block having a pair of solid lines illustrating fluid paths 64, 66 which are normally connected or conductive to fluid when the valve is in its normal or deenergized state, along with dashed lines depicting flow paths 70, 72 which are normally not connected and not conductive to fluid when the valve is in its normal, deactivated, or deenergized state. Thus, the port 60 is connected by the path 64 to a port 74 and a port 76 is connected by path 66 to a port 78 when the valve is deenergized as shown in FIG. 2. On the other hand, ports 60, 78 are interconnected by the path 70 and ports 74, 76 are connected by the path 72 when the valve is activated or energized in response to an electric signal applied at a terminal 80a. It should be noted that the ports 60, 74, 76, 78 may act either as inlets or outlets without regard to whether the valve is in its operated or unoperated state. The valve 62, along with other similar valves herein, is designed to be resiliently urged into the inactivated state by a suitable means such as a spring so that all flow will stop in the event of a power failure, or in the event of detecting air in the blood by the air detectors 48, 50 (in a manner to be described hereinafter). The valve 62 (and other similar valves) may be a pneumatically actuated valve, the pneumatic actuation in turn being in response to an electrically operated solenoid valve. Valves of this type are made by several manufacturers and are available in the marketplace.

The port 74 is connected by tubing 82 to an I.V. source and pump apparatus 84 which may be of any conventional type used for irrigation and/or infusion purposes. With the valve 62 deenergized as shown in FIG. 2, the I.V. source and pump 84 is connected through the valve 62, the air detector 50, the connector 44 and the oximeter 36 to the connector 32 for fluid communication with a catheter. When valve 62 is energized, blood is withdrawn from the patient and I.V. solution from 84 is exhausted to waste through port 76 and conduit 112. In this way no damage to the system results which would otherwise threaten because of pressure forces. The I.V. source and pump 84 may be used to infuse intravenous solution into the patient through the catheter at 32.

The air detector 48 is connected by tubing 86 to a port 88 of a valve 90, another port 92 of which is connected by tubing 94 to the port 78. A port 96 is connected by tubing 98 to a pressure transducer 100, a single path valve 102, and a flow restrictor 104. The valve 102 may be actuated at 103 to conduct fluid by manual application, so as to use the saline source 110 with a high flow rate for flushing out various lines. However, this forms no part of the invention herein, except to illustrate the versatility thereof. The pressure transducer 100 can be of any type well known for the purpose of deriving the patient's blood pressure, and provides an electrical signal indicative thereof at an output terminal 106. This signal may be utilized in any well known fashion, and the transducer forms no part of the present invention. The valve 102 and flow constrictor 104 are connected by tubing 108 to an 8 psi saline solution source 110. With the valve 102 closed as shown, the flow constrictor 104 will provide a very minute, constant, low-pressure flow of saline to the tubing 98 which may be used as a constant flush system to prevent clotting at the end of the catheter connected to the connector 32 during prolonged use, between withdrawal cycles. It should be noted that this function of the apparatus is unnecessary when irrigation is being regularly provided from the I.V. source 84, as described hereinbefore. Therefore, the saline from the source 110 is normally passed by valves 90, 62 through the port 76 and a suitable means 112 to waste. The means 112 may comprise tubing leading to a waste bucket, or it may simply comprise a syringe attached directly to the port 76.

The valve 90 includes a port 114 connected by tubing 116 to a port 118 of a valve 120, which includes a port 122 connecting with a means 124 leading to a blood cup which is described hereinafter with respect to FIG. 3. The means 124 may otherwise comprise tubing leading to any receptacle for blood, or a syringe to receive blood which may be attached directly to the port 122. The valve 120 also includes a port 126 leading to tubing 128 which is provided in sufficient length (such as by inclusion of loops 130 therein) to serve as a reservoir on the order of two milliliters in capacity. The other end of the tubing 128 is connected to a port 132 of a valve 134 which includes a port 136 connected by tubing 138 to a constant volume pump 140. The exact nature of the constant volume pump is immaterial to the present invention with the exception of the fact that if the pump 140 provides a constant known volume of fluid per unit of time that it is actually actuated, the volume displacement for a complete stroke also will be constant. However, the pump 140 may comprise a syringe driven by a piston within a cylinder, the piston in turn being driven by air supplied thereto over tubes 142, 144 under control of a valve 146 which is connected by a tube 148 to a source 150 of air at 30 psi (for instance). The valve in turn is responsive to an OR circuit 152 so that it will be actuated in response to signals applied on a terminal 154 or on a terminal 156. With the valve 146 deactivated as shown, air is applied over the tube 144 to cause a cycle which pushes blood from the pump 140; when the OR circuit 152 is energized by a signal on either of the terminals 154, 156, it activates the valve 146 to apply air pressure from the source 150 to the tube 142 and cause a cycle which draws fluid into the pump 140. The valve 120 may be activated by a signal from an OR circuit 158 in response to electric signals at either of two terminals 160, 80c. Provision of the OR circuits 152, 158 permits operation of the pump 140 and the valve 120 in response to diverse controls; similarly, the valve 134 is actuated in response to an electric signal from an OR circuit 162 which in turn may operate in response to electrical signals applied on either of two terminals 164, 80d, in a manner which is described in detail hereinafter with respect to FIGS. 4 and 5. Briefly, by actuating the valves 62, 90, 120 and 134 by the simultaneous application of electric signals to terminals 80a, 80b, 80c, and 80d, the air detector 50 (and therefore a catheter connected to the connector 32) will be connected to the pump 140, and the I.V. source 84 will be vented through the path 72 to waste. This enables making a short stroke with the pump 140 so as to draw blood into the oximeter 36 for the purpose of monitoring blood oxygen saturation, which can be done frequently with substantially no blood loss or interruption of any other functions; such a test is extremely useful, when performed on a frequent, cyclic basis, to provide an indication of when a more complete blood analysis may be required.

The valve 134 includes a port 166 connected by tubing 168 to a saline reservoir 170; this is used, as is described more fully hereinafter with respect to FIGS. 4 and 5, to aid in the withdrawal of blood from (and return of a portion of the blood to) the patient, the insertion of some of the blood in the blood cup for analysis, and in washing out the system. Preferably, the reservoir 170 takes the form shown in FIG. 6, i.e. a constant diameter small bore tubing 170' coiled about a suitable retainer such as the cylindrical retainer 171. The tubing 170' presents a female port 173, through which additional saline may be introduced to replenish the supply. This configuration has been found to solve the heretofore substantial problem of blood/fluid interface mixing. By restricting the blood/saline interface, infused saline is minimized.

The valve 134 also has a port 172 which is shown connected to a connector 174 having a plug 176 therein. The port 172 may advantageously be used with a manual flush syringe, if desired.

The valve 120 is provided with an additional port 178 which is connected to connector 180 blocked off by a plug 182. The connector 180 may be used to facilitate connection to the valve 120 of pressure transducer apparatus and saline flush apparatus similar to the apparatus 98-110 described hereinbefore. With such an arrangement, constant flush may be provided through the valves 90, 120, when deenergized as shown, and through the air detector 48 to the catheter connected to the connector 32. Then, if desired, a second catheter may be connected to the connector 44 (disconnecting the tube 46 from the tubing 42) so as to allow the running of two systems simultaneously, the catheter connected to the connector 44 being operable either in conjunction with a constant saline flush or in conjunction with an I.V. irrigation, as described hereinbefore, in dependence upon the setting of the valve 62. This illustrates the versatility of the present invention.

It is sometimes desirable to fit the influent end of the withdrawal unit with an alarm, so that when blood unexpectedly appears, the attendant is promptly notified. Such an alarm would be shut off during intentional withdrawal of blood.

Figure 3:
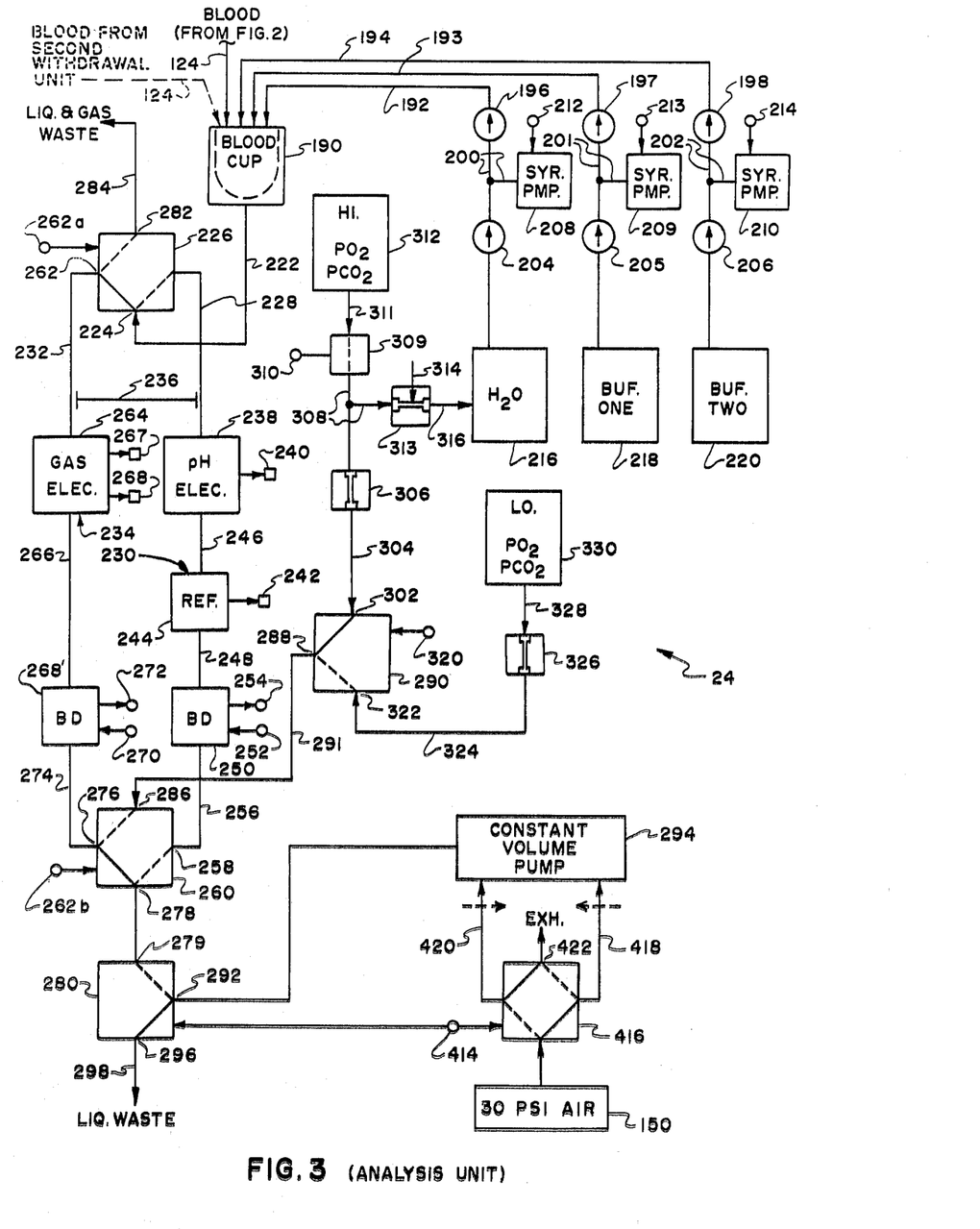
FIG. 3 is a schematic block diagram of an automated blood analysis unit in accordance with the present invention.

Referring now to FIG. 3, an embodiment of an analysis unit 24 in accordance with the present invention includes a blood cup 190 which may receive blood manually from a syringe, or by being properly disposed may receive blood by other means 124 (FIG. 2) from one withdrawal unit. The blood cup 190 represents a distinct interface between the withdrawal unit and the analysis unit permitting blood to reach the analyzer by force of gravity but preventing analyzer fluids from reaching the patient by maintaining a distinct physical separation between the units. Thus, the analyzer fluids (calibration gases and liquids) and the components of the analyzer need not be sterile. As a result all constraints required by a sterile analyzer are removed and the analyzer may be used on one patient after another without appreciable time delay.

In addition, the blood cup 190 may receive a water washout solution over tubing 192, and either of two buffer solutions over tubing 193, 194. The tubing 192-194 is connected to respective check valves 196-198 which are in turn connected by respective tubing 200-202 to additional check valves 204-206 and to corresponding syringe pumps 208-210. The pumps 208-210 provide a push stroke in response to electric signals applied to corresponding terminals 212-214. The volumetric capacity of the pumps in such that upon release of the signals on terminals 212-214 the pumps provide draw cycles through the check valves 204-206 to supply the desired amount of fluid to be driven through the check valves 196-198 upon the next energization of the pumps by the application of electric signals at the terminals 212-214. The check valves 204-206 are connected to a source 216 of water and to sources 218, 220 of two different buffer solutions. The buffer one solution in the source 218 may comprise a dilute solution of $Na_2 HPO_4$ and $KH_2 PO_4$ having a pH of about 7.45, and the buffer two solution in the source 220 may be a dilute solution of $Na_2 HPO_4$ and $KH_2 PO_4$ having a pH of about 6.88. The two different pHs allow for two calibration points on a pH test as described hereinafter.

The blood cup 190 is connected by tubing 222 to a port 224 of a valve 226 which alternatively connects the blood cup 190 to a tubing 228 of a pH tester 230 and through tubing 232 connected to a blood gas tester 234. An important feature of the present invention, which is described more fully with respect to FIGS. 4 and 5 hereinafter, is the utilization of the pH tester 230 to check the blood gas tester 234 for leaks. In order to achieve this, a means 236 is provided to insure that the liquid in the tubing 228 and in the tubing 232 are at the same electrical potential. The means 236 illustrated in FIG. 3 may comprise a stainless steel wire which passes through the walls of the respective tubing 228, 232 so as to provide for an electrical conduction therebetween. On the other hand, depending on the nature of the valve 226, it is possible that in some utilizations of the present invention the electrical conductivity can be maintained by means of wetness of the surface within the valve 226, without regard to whether the valve is actuated or not.

The tube 228 provides fluid connection to a pH electrode 238 which may be of any conventional known type that provides an electric signal at an output 240 which, in conjunction with a reference electrode signal at an output terminal 242 provides a measure of the pH of the fluid, therein. The electric output terminal 242 is connected to a reference electrode 244 of the type known in the art, which may be connected by tubing 246, or in any other suitable fashion, to the primary electrode 238. The reference electrode 244 is connected by tubing 248 to a blood detector 250 which may be of any conventional type, such as a photodetector system which senses the opacity of the fluid therein, thereby recognizing the difference between blood and either gas or saline solution. The blood detector 250 is provided with an electric current applied over an input terminal 252 to operate a light source therein, and the photodetector therein provides an electric signal at an output terminal 254 which is a measure of the transmissivity of the fluid flowing therein. Since this is of conventional nature and forms no part of the present invention, further description is not given herein. The sensing of the blood/fluid interface at blood detector 250 and/or blood detector 268' controls the positioning of blood which is pulled from the cup and accordingly, the needed volume of blood. If blood is not sensed within a predetermined time, an error is indicated, measurement is terminated and the system is flushed. In this way the amount of blood used by the analyzer and not returned to the patient is minimal. The blood detector is connected by tubing 256 to a port 258 of a valve 260 which is always operated in conjunction with the valve 226 by simultaneous application of electric operating signals to a pair of input terminals 262a, 262b, as is described more fully hereinafter.

The tubing 232 is connected to gas electrodes 264 which provide electric signals at a pair of output terminals 267, 268. The gas electrodes may be conventional membrane-type electrodes for measuring $PO_2$ and $PCO_2$, and form no part of the present invention. The gas electrodes 264 are connected by tubing 266 to a blood detector 268' which is similar to the blood detector 250 including an electric input terminal 270 and an electric output terminal 272. The blood detector 268' is connected by tubing 274 to another port 276 of the valve 260. When deenergized, the valve 226 provides flow of blood from the blood cup 190 into the blood gas detector 264 and through the port 278 to port 279 of a pump valve 280. When energized, the valve 226 connects the blood cup 190 to the pH tester 230 and connects the gas detector 234 through a port 282 to tubing 284 or other suitable waste disposition means. When the valve 226 is energized, the valve 260 is also energized, connecting the pH tester 230 through the port 258 of valve 260 to port 279 of the pump valve 280, but also connecting the gas tester 234 through ports 276 and 286 of valve 260 to a port 288 of a calibration gas valve 290 by a tubing 291. The pump valve 280 includes a port 292 connected to a constant volume pump 294 and a port 296 connected by a suitable tubing 298 or other means to a proper disposition for liquid waste.

The port 288 of the valve 290 is normally connected through a port 302 and tubing 304 to a flow constrictor 306 which in turn is connected by tubing 308, a valve 309 (operated by a signal at a terminal 310), and tubing 311 to a source 312 of a high $PO_2$ and $PCO_2$. The tubing 308 also applies such to a variable flow constrictor 313 which is provided with a manual adjustment 314 to adjust the amount of flow therethrough. This provides gases from the source 310 to the water source 216 over tubing 316, thereby to provide sufficient carbonate in the water of the source 216 so that the gas electrodes 264 will, after being washed with water from the source 216, have a substantial carbon dioxide concentration diffused through the membranes prior to a final calibration of the unit. That is, in the process of using calibration gas to drive washout water through the unit, the concentrations will not be so depleted in the gas electrodes 264 so as to require an undue equilibration time for a final test after all blood is washed therefrom.

The valve 290, when activated by an electric signal at an input terminal 320, connects its port 288 with a port 322 and tubing 324 to another flow restrictor 326 which is connected by tubing 328 to a source 330 of low $PO_2$ and $PCO_2$. Since the sources 312, 330 are under pressure, they are used, as described hereinafter, in the process of cleaning out the gas electrodes 264. The analyzer is calibrated before blood is introduced. Specifically, a liquid calibration fluid is used to calibrate pH electrode 238 and a gas calibration fluid is used to calibrate gas electrodes 264. Thereafter, the calibration fluids are retained in the analyzer and used, responsive to negative pressure, to displace blood within the analyzer after it is received at cup 190. In this way the calibration is preserved.

Figure 4:
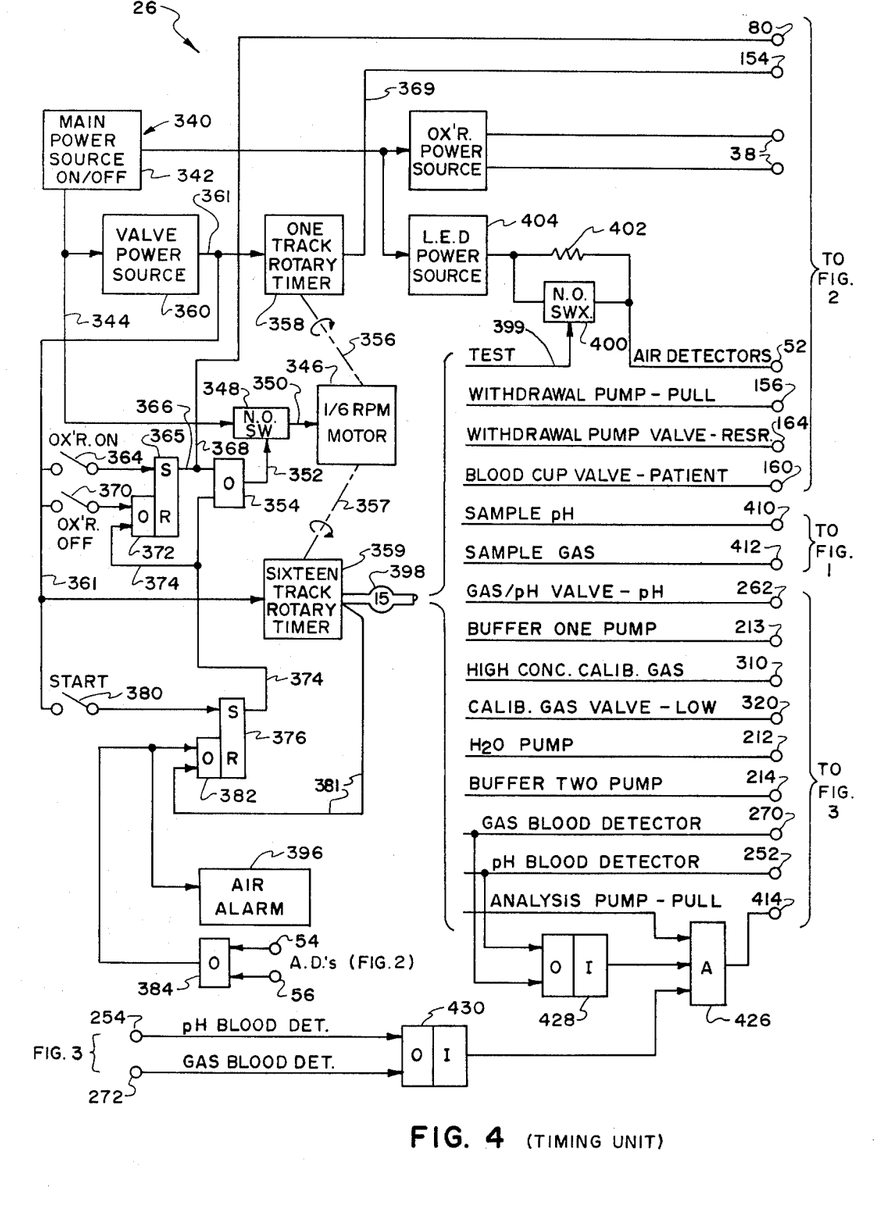
FIG. 4 is a simplified schematic block diagram of a timing unit which may be used in conjunction with the embodiment of the invention illustrated in FIGS. 2 and 3.

Referring now to FIG. 4, the timing unit 26 includes some source of ordinary power 340 which is assumed to include means 342 for turning it on and off. Such power may simply comprise 60 cycle 120 volt power. The source 340 is connected by a line 344 to a one-sixth revolution per minute motor 346 through a normally open switch 348 and a line 350. The switch 348 is normally open and must be activated by a signal on a line 352 from an OR circuit 354 in order to apply power from the line 344 to the motor 346. The motor is connected by shafts 356, 357 to a one track rotary timer 358 and a sixteen track rotary timer 359. The timers 358, 359 are supplied power from a valve power source 360 over a line 361. When it is desired to run the withdrawal unit for periodic oximeter testing only, an oximeter ON switch 364 may be closed applying power from the line 361 to a set input of a latch 365 which provides a signal on a line 366 to operate the OR circuit 354 and apply power to the motor 346. At the same time, the signal on the line 366 applies power to the terminal 80 which in turn is applied in FIG. 2 to all of the terminals 80a–80d. This connects the constant volume pump 140 (FIG. 2) through the valves 62, 90, 120 and 134 to draw blood through the air detector 50 and the oximeter 36 for the purpose of testing the oxygen saturation of the blood. Within the one track timer 358, a single contact element per revolution is provided, so as to provide a signal on a line 368 to the terminal 154 which will cause the OR circuit 152 (FIG. 2) to operate the valve 146 and initiate a short stroke of the pump 140. For instance, the length of the signal on the line 368 (and therefore the length of time duration of the pump stroke) may be approximately eight seconds so as to draw approximately 0.5 of a milliliter of blood through the oximeter 36, and then restore it back to the patient. This is readily achieved by providing a contact in the timer 358 which extends over eight degrees (the same number of degrees as is desired seconds since the 1/6 rpm motor 346 will cause the timer to complete one revolution in 360 seconds — 6 minutes). Because of its simplicity, the internal structure of the timer 358 has not been shown. Once the switch 364 is closed, the testing of the blood in the oximeter will continue cyclically until it is desired to cease, which is achieved by depressing an oximeter OFF switch 370. This causes an OR circuit 372 to reset the latch 365 so as to remove power from the line 368, thereby deenergizing the terminal 80 to return the valves in FIG. 2 to their unenergized state, and causing the switch 348 to resume its normally open condition so that no more power is applied to the motor 346.

Additionally, the OR citcuit 354 may be operated by a signal on a line 374 in response to the setting of a bistable device such as a trigger or latch 376 whenever full automatic withdrawal and analysis cycles are being performed under the control of the sixteen track rotary timer 359. The sixteen track timer 359 has sixteen tracks of contacts which are arranged as shown in FIG. 5. If the timer 359 is a drum timer, then FIG. 5 depicts the contact arrangement simply by joining the left end thereof (zero seconds in time and zero arcuate degrees) with the right end thereof (360 seconds in time and 360 arcuate degrees). On the other hand, if the sixteen track timer 359 is arranged in the form of a disc, then it may be profitable to provide on the radially inward tracks those contacts which are very small and do not consume much space whereas the larger contacts, or ones that have to be extremely accurate, may be placed on the radially outward tracks, all as is well known in the rotary shaft encoder art. Power to the contacts within the timer 359 is supplied by the line 361. Starting a full withdrawal and analysis cycle is achieved by setting the latch 376 by means of depressing a START button 380, which will cause the latch 376 to remain energized until the end of the complete cycle, which occurs at about 355 seconds after initializing by the generation on a motor control line 381 of a signal which indicates that the cycle is complete. This is applied to an OR circuit 382 which causes resetting of the latch 376. The OR circuit 382 will also be operated by an OR circuit 384 in response to signals at either of a pair of terminals 54, 56 (FIG. 2) indicating that air bubbles have been detected in the blood lines. The OR circuit 384 may also operate an alarm 396 so as to advise an attendant at an intensive care nurses' station or otherwise that air has been detected in the lines. While the rotary timer 359 is operating, it presents signals on a plurality of lines to operate valves and pumps so as to cause direct cyclic operation of both the withdrawal unit and the analysis unit for a complete automatic withdrawal and sampling of blood, together with washout and calibration thereof. Each of the lines at the output of the rotary timer, depicted as being within a trunk of fifteen lines 398, is provided with an appropriate legend, and is connected to the electric terminal which it operates in FIGS. 1, 2 or 3.

Specifically, the signal lines 398 from the sixteen track timer 359 include a signal causing a test of the air detectors on a line 399, which operates a normally-open switch 400 to short-circuit a resistor 402, so as to provide more current from an LED power source 404 through the terminal 52 to the air detectors 48, 50 (FIG. 2). This over-powers the air-detectors and forces an alarm condition even though there is liquid in them, unless they are inoperative.

The air detector and its operation form no part of the present invention; however, it should be obvious that combination of the signal on the line 52 and a lack of signals on the lines 54, 56 could operate an OR circuit similar to the OR circuit 384 to create an alarm condition which could turn off the latches 365 and 376 and operate the alarm 396 if the air detectors are not working. A withdrawal pump signal which causes the withdrawal pump 140 (FIG. 2) to initiate a pull stroke, thereby drawing blood into the system from a catheter, is provided to the terminal 156. A withdrawal pump valve signal at terminal 164 operates the valve 134 (FIG. 2) in such a fashion as to connect the pump to the two milliliter reservoir 130. A blood cup valve signal applied to a terminal 160 causes the valve 120 (FIG. 2) to operate so as to connect the two milliliter reservoir 130 to the patient (port 118) rather than to the blood cup. A sample pH signal is applied to a terminal 410 to indicate to any apparatus, such as the calculation unit 28 of FIG. 1, that now is the proper time to sample the output of the pH tester 230 (FIG. 3) at the terminals 240, 242. Similarly, a sample gas signal is applied to a terminal 412 to indicate to the calculation unit 28, or such other unit as may be used to analyze the results of blood tests, that now is the proper time to sample the output of the gas tester 234 at the terminals 267, 268. A gas/pH valve signal applied to the terminal 262 in FIG. 4 is connected to both of the terminals 262a and 262b (FIG. 3) so as to cause simultaneous operation of the valves 226, 260 so as to transfer primary operation from the gas side to the pH side. A buffer one pump signal applied to a terminal 213 causes the buffer one syringe pump 213 to stroke in the push direction. A high concentration calibration gas signal applied to a terminal 310 causes closure of the valve 309 (FIG. 3) to allow the high concentration calibration gas source 312 to enter the system. The calibration gas valve signal applied to a terminal 320 causes the valve 290 (FIG. 3) to transfer from the normal high concentration connection, as shown, to connect the low concentration source 330 with the port 288. An $H_2O$ pump signal connected to a terminal 212 causes the syringe pump 208 (FIG. 3) to initiate a push stroke. A buffer two pump signal applied to a terminal 214 causes the syringe pump 210 (FIG. 3) to initiate a push stroke. A gas blood detector signal applied to a terminal 270 powers a light source in the blood detector 268' (FIG. 3) so as to be able to detect the presence of blood. Similarly, a pH blood detector signal applied to a terminal 252 energizes the blood detector 250 (FIG. 3) so as to be able to detect blood passing therethrough.

An analysis pump signal is applied to a terminal 414 for application to the valve 280 (FIG. 3) and to a related valve 416 which is connected in an obvious fashion by tubings 418, 420 to the pump 294. Thus, with the signal present at the terminal 414 the valve 280 will connect the valve 260 to the pump 294, and the valve 416 will cause the pump 294 to initiate a pull stroke pulling fluid through the valve 292 into the pump 294; at this time, operating air within the pump is exhausted through the tube 418 and the valve 416 through a port 422 to exhaust. Upon removal of the signal on the terminal 414, the valve 280 connects the port 292 with the port 296 and the valve 416 drives air through the tubing 418 to cause a push stroke of the pump 294, while operating air therein is transferred through the tubing 420 and the port 422 to exhaust. Thus, the pump 294 always draws fluid into itself from the valve 260, and thereafter pushes that fluid through the port 296 of the valve 280 to liquid waste.

The signal on the terminal 414 is generated specially in FIG. 4 by means of an AND circuit 426 in response to an OR circuit 427 operated by either one of two OR-invert circuits 428, 430. These circuits are normally operative because there is normally no signal present at the terminals 270, 252 so that the blood detectors are inoperative, and there is also no signals at their output terminals 254, 272. However, once the blood detectors are activated by signals at terminals 252, 270 these signals preclude the OR-invert circuit 428 from any longer providing a signal to the OR circuit 427. But if no blood is detected in the blood detectors, then there will still be no signals at the blood detector output terminals 254, 270 (FIG. 3) so that the related OR-invert circuit 430 will operate the AND circuit 426 to provide a signal at the terminal 414 for the operation of the pull stroke of the analysis pump 294 (FIG. 3). However, once blood is sensed by either of the blood detectors, a signal on either of the terminals 254, 272 will cause the OR-invert circuit 430 to remove the input to the OR circuit 427, thus terminating the stroke of the pump 294 (FIG. 3). Use of the OR invert circuit 428 precludes the possibility of noise or other spurious signals from blocking the AND circuit 426 when the blood detectors are not turned on. This feature allows drawing just a requisite amount of blood into the pH tester 230 and the gas tester 234 so the blood isn't drawn through other parts of the system thereby necessitating a greater amount of blood and washout.

Figure 5:
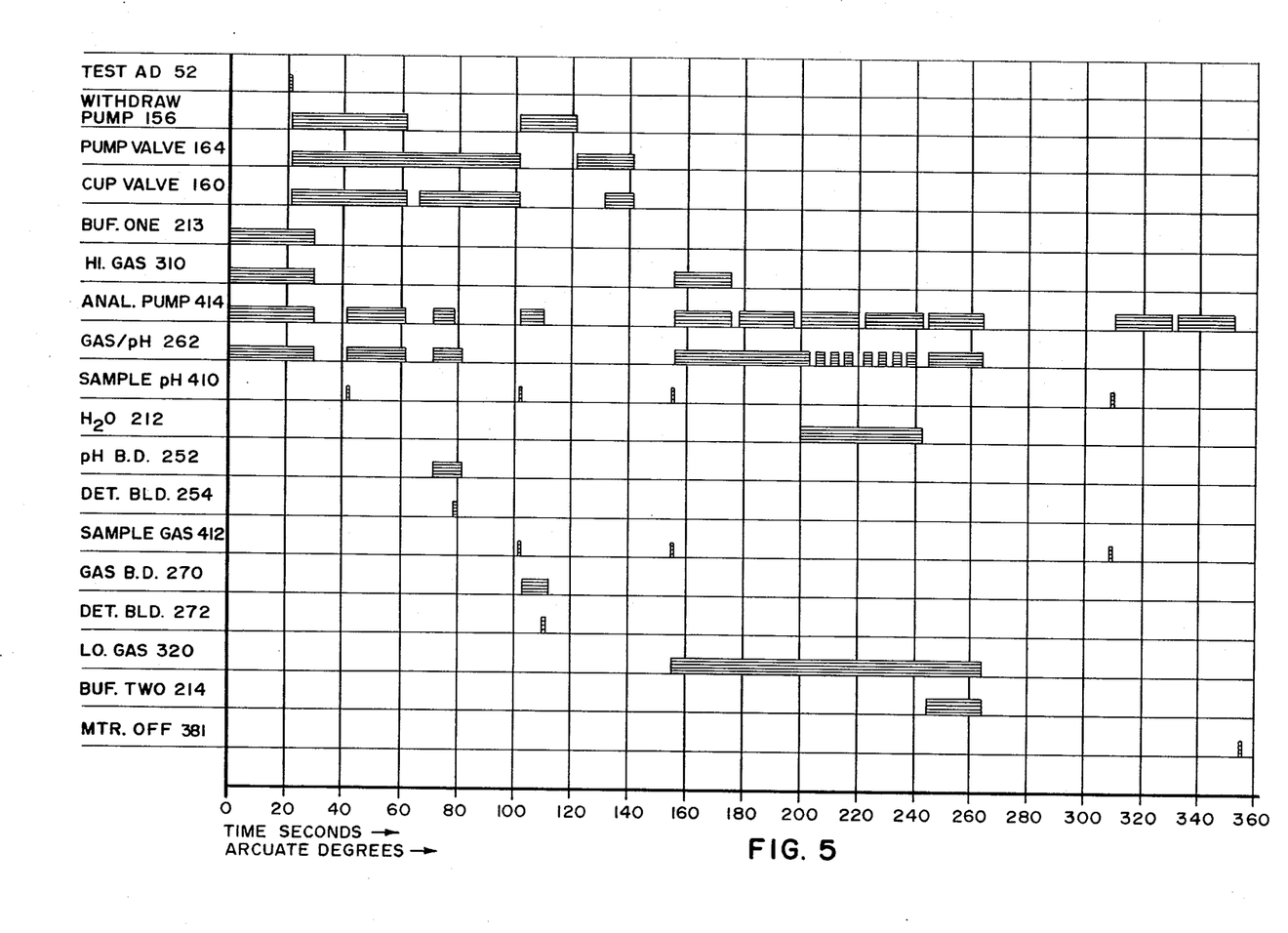
FIG. 5 is a diagram illustrating a mode of cyclically timing the apparatus of the embodiments of FIGS. 2 and 3.
Figure 6:
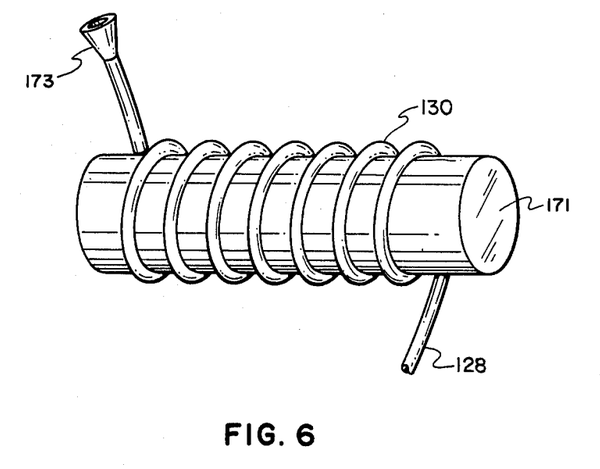
FIG. 6 is a perspective representation of a preferred fluid reservoir.

Operation of the device, as illustrated in FIG. 5, begins with the main power source turned on by the depression of the start switch 380 (FIG. 4) which will cause the latch 376 to become set, overriding a tendency of the OR circuit 382 to reset it, thereby closing the normally open switch 348 so as to apply main power to the 1/6 rpm motor 346. The switch should be depressed for at least a second until the motor can turn sufficiently so as to clear the motor control segment and thus remove the signal on the line 381 so that the motor will continue to run. Then, at time zero, signals are applied to the terminals 213, 310, 414 and 262 so as to energize the buffer one pump, close the high concentration gas valve, start the analysis unit pump 294 and place the gas/pH valve to the pH side. This causes buffer one to be pushed into the blood cup 190 and drawn by the constant volume pump into the pH tester 230 all the way into the pump 292, while high concentration calibration gas flows into the gas tester 234. All of these signals remain present for thirty seconds. However, after the first second, the air detectors in the withdrawal unit (FIG. 2) are tested. Thereafter, at the twenty-first second, signals are applied to terminals 156, 164 and 160, and the pump in the withdrawal unit (FIG. 2) is actuated at the same time that the pump valve and cup valve are actuated so as to draw blood from the catheter through the connector 32 through the oximeter and the air detector into the port 88 of valve 90 through the valve 120 and into the two milliliter reservoir 130. These conditions are maintained for forty seconds, until about the sixty-first second, although the pump valve 134 is left in the actuated position to connect the two milliliter reservoir to the pump all the way to the one hundred first second. While the blood is being drawn into the withdrawal unit, at about the twentieth second, all of the elements in the analysis unit are turned off and there is a ten second equilibration period where buffer one is allowed to equilibrate within the pH tester 230. Thereafter, at about the fortieth second, the pH is sampled at the terminal 240 so as to provide a first calibration measurement of the pH detector 230. As soon as this is complete, at about the forty-first second, buffer one is flushed out of the pH tester 230 by energizing the water pump (terminal 212), reactivating the gas/pH valve so as to feed pH (terminal 262), and reactivating the pump (terminal 414) for a full cycle so that as water or saline falls into the blood cup, it is drawn all the way down into the pump. These signals (terminals 212, 262 and 414) are maintained energized for about twenty seconds until about the sixty-first second.

At the sixty-first second, in the withdrawal unit, the signal on terminal 156 and that on terminal 160 are removed so that the withdrawal pump will initiate a push stroke with the valve 120 deenergized so that blood is pushed from the two milliliter reservoir 130 into the blood cup. At this time, everything in the analysis unit is deenergized and remains so for approximately ten seconds to allow the blood to settle down in the blood cup. The valve 120 is actuated after about seven seconds (which permits pumping substantially 0.4 milliliters into the blood cup) and then it is energized so that the remainder of the blood will be returned to the patient along with approximately 1.5 milliliters of saline. It is to be noted that, prior to starting the operation, saline existed in the lines as a result of initially loading them or as a result of finishing the prior cycle as is described hereinafter.

After allowing ten seconds for the blood to settle in the cup, at about the seventy-first second, the blood detector 250 is turned on by a signal on terminal 252, and blood is drawn into the pH tester by applying signals to the terminals 262 and 414 so that the gas/pH valve is in the pH position and the pump will initiate a pull cycle. However, as soon as blood reaches the blood detector 250, it will cause (by means of the apparatus at the bottom of FIG. 4 described hereinbefore) deenergization of the signal at the terminal 414 so that the pump stroke stops immediately. This prevents pulling any unnecessary amount of blood beyond the reference electrode 244. This will occur in something on the order of eight seconds, and at the end of ten seconds the blood detector valves 226 and 260 and the primary initialization signal for the pump 292 are all deactivated. This occurs at approximately the eighty-first second. Then twenty seconds of equilibration time is allowed to elapse. During this time, the remainder of the blood in the analysis unit has been returned to the patient; it should be understood that since the pump 140 is a constant volume pump, regardless of the energization thereof, the volume of fluid to be returned to the patient is determined simply by the length of stroke so that the pump and relay circuits in the withdrawal unit are energized simply for a long enough period of time to allow the pump to complete its stroke. This occurs at approximately the one hundred and first second.

At this time, the blood in the pH tester 230 is still equilibrating, as is the high concentration calibration gas which entered the gas tester 234 at time zero. At the one hundred and first second or so, the pump in the withdrawal unit (FIG. 2) is caused to make a pull stroke with the valve 134 disenergized to pull saline solution from the source 170 down into the pump. At the same time (one hundred and first second) the pH and gas detectors are both sampled at the output terminals 240, 242 and 267, 268. This comprises a first test of the pH of the blood itself and a first calibration test of the gas electrodes 264. Following that, at the one hundred and second second, the gas blood detector 268' is turned on with a signal at the terminal 270 and the pump is started by applying a signal on the line 414. This action draws blood from the blood cup 190 down through the gas tester 234 until the blood reaches the blood detector at which time a signal appears on terminals 272 which, through the apparatus at the bottom of FIG. 4, removes the signal on line 414 and stops the blood pull stroke. Then there is a forty-five second equilibration period where everything in the analysis unit (FIG. 3) is turned off. However, at the one hundred and twenty-first second, flushing of the withdrawal unit (FIG. 2) begins by shutting off the signal on line 156 to the pump so that the pump will commence a push cycle and energizing the valve 134 so that the push will be in the direction of the two milliliter reservoir 130. This starts saline (which has just been withdrawn from the reservoir 170) to flow through the two milliliter reservoir 130 and through the deenergized valve 120 into the blood cup or waste receptacle. However, after ten seconds, the valve 120 is energized so that the remainder of the saline then flows upwardly through the valve 90, the air detector 48 and oximeter 36 toward the catheter. This insures that the lines in the withdrawal unit are left with saline in them (as referred to hereinbefore).

Following a forty-five second equilibration period with blood in the gas detector 234, both the gas and pH are sampled at their terminals 240, 242 and 267, 268 which comprise the first sampling of gas in the blood itself and the second sampling of pH in the blood. The second sampling of pH is to provide an indication of the integrity of the gas electrodes 264; if there is any leakage in the gas electrode 264, such a leak would cause a change in the electrical potential of the blood in the tubing 232, and because of the stainless steel electrical connector 236 between that tubing and the tubing 228, it would also result in a change in the electrical potential of the blood within the pH electrode 238. This would result in a different pH reading than that which was previously obtained. Utilization of a second pH reading of the blood is achieved by calculations performed in the calculation unit 28 (FIG. 1) or in a computer if one is used, or simply a substantial difference in pH reading indicates to the operator that there is likely to be a fault in the gas electrodes 264. This is an important feature of the present invention.

After sampling the pH and gas electrodes, at about the one hundred and fifty-sixth second, flushing of the blood from the pH tester 230 and the gas tester 234 commences. This is achieved by closing the high gas relay 309, energizing the high/low gas valve 290 so that the low concentration calibration gas is available, energizing the gas/pH valves 226 and 260 so as to permit flow into the pH side and starting the pump by applying a signal to the terminals 414. The high gas valve 309 is closed to permit leakage of gas from the source 312 into the water source 216 so as to increase the carbon content thereof. At the same time, saline is drawn from the blood cup 190 down into the pH tester 230. These conditions continue until about the one hundred and seventy-sixth second. At that time, the high gas valve 309 is closed and the pump is turned off so that it makes a push stroke with the valve 280 deenergized, pumping blood and perhaps some saline to liquid waste through the port 296. After two seconds (at the one hundred and seventy-eighth second), the pump is again turned on drawing more saline into the pH tester 230; during this entire period of time (from the one hundred and fifty-fifth second) the low concentration calibration gas in the source 330 has been passing through the valve 290 and the valve 260 upwardly through the gas tester 234 and through the valve 226 upwardly through the port 282 driving blood to waste. At about the one hundred and ninety-eighth second the pump is again shut off for two seconds and it pushes the blood and saline which it has drawn from the pH tester 230 outwardly through the port 296 of the valve 280 to waste. At the two hundredth second, the $H_2O$ pump is again energized (212) to cause water to be pushed into the blood cup. The analysis pump is again started at about the two hundredth second and again draws saline and water through the pH detector for three seconds, then the valves 226 and 260 are turned off for two seconds so that the pump, instead, draws saline and water into the gas detector 234. After two seconds the valves 226 and 260 are again energized so that saline is drawn into the pH detector, and while this is occurring, the low concentration calibration gas in the source 330 pushes some of the saline out of the gas detector 234 upwardly through the port 282 to liquid waste. This process continues until about the two hundred and twentieth second when the pump is turned off so that it provides a push stroke to push all the waste it has collected from both the pH tester 230 and the gas tester 234 outwardly through the port 296 to waste. The procedure is again repeated so that at approximately the two hundred and forty-second second the pump again discharges waste that it has collected from both the pH tester 230 and the gas tester 234, during which time the valves 226 and 260 have cycled, and while in the energized position the low concentration calibration gas of the source 330 has pushed waste upwardly out of the gas tester 234. At about the two hundred and forty-fourth second, the pump and the pH/gas valve are again turned on at the same time as the buffer number two pump is turned on so that buffer number two begins to be pumped into the blood cup 190 and this is drawn into the pH tester 230. This is completed twenty seconds later, at about the two hundred and sixty-fourth second. During this twenty second period, the low concentration calibration gas of the source 312 has been continuously running into the gas tester 234 and venting outwardly through the port 282 to waste. Thus at the two hundred and sixty-fourth second, the pH tester 230 is filled with buffer number two and the gas tester 234 is filled with low concentration calibration gas from the source 330. An equilibration period of forty-five seconds then passes following which, at the three hundred and ninth second, both pH and gas are again sampled at their terminals 240, 242 and 267, 268 for a final calibration of both the pH and gas testers 230, 234. The calibration provides corrections for changes in sensitivity and drift of the electrodes.

All that now remains is to purge the calibration gas out of the gas electrode and leave the gas electrode filled with water so as to prevent the membranes therein from drying out. It is to be noted that the pH electrode is left with buffer number two residing therein which prevents it from drying out. The loading of water and purging of gas in the gas electrode 264 is accomplished, beginning at the three hundred and tenth second, by energizing the water pump by means of a signal at the terminal 212 so as to commence to pump water into the blood cup 190 at the same time that the pump is operated by providing a signal at the terminal 414 while leaving the valves 226 and 260 deenergized so that the clean water is drawn into the gas tester 234. After twenty seconds, the pump is deactivated for two seconds to allow dumping the mixture of gas and water out to liquid waste, following which it is again activated to pump the remaining water out of the blood cup 190 into the gas tester 234. This completes the operation of the cycle and the motor is caused to shut off at about the three hundred and fifty-fifth second by generating a signal on the motor control line 380 which activates the OR circuit 382 to reset the latch 376, thereby removing the signal from the normally open switch so that the motor no longer receives power. The motor will therefore stop when the sixteen track rotary timer is set on the contact that provides the motor control signal on line 381.

The embodiment of the invention described hereinbefore thus provides a very compatible blood withdrawal unit which, according to the invention, may withdraw blood through lines filled with saline so as to preserve the integrity of tests to be performed on blood, or may withdraw blood through lines filled with I.V. irrigation solutions, thereby to minimize the opportunity for sodium buildup in the patient. In addition, the described embodiment provides for final calibration of gas and pH testers after testing of blood, in addition to initial calibrations before the testing of blood. By providing a dual test of blood pH, one without fluid in the gas detector and one with fluid in the gas detector, together with providing for an electrical connection between the gas and pH testers, the dual pH tests provide a measure of the integrity of the gas tester. Carbonation of washout water in the gas tester provides for the preestablishment of a certain level of carbonate in the gas detector to reduce the time necessary for equilibration thereof, and in further accord with the invention, valving between the pH tester and the gas tester permits simultaneous washout utilizing a single pump, in combination with the use of calibration gas to completely flush, forwardly and backwardly, the gas electrode, while simultaneously performing a forward flush of the pH electrode.

Although the invention has been shown and described with respect to a preferred embodiment thereof, it should be understood by those skilled in the art that various changes and omissions in the form and detail thereof may be made therein without departing from the spirit and the scope of the invention.

Having thus described typical embodiments of our invention, that which we claim as new and desire to secure by Letters Patent is:

1. An automated blood unit to provide a fool proof safety check against calibration drift comprising:
    a blood gas tester;
    a blood pH tester;
    fluid source means providing a source of blood, a source of blood gas test calibration gases, and a source of blood pH test calibration buffer solution; and
    means including pumps and valves and operable in response to a controlled program to calibrate said gas tester and said pH tester by applying calibration fluid thereto and sampling the readings thereof, immediately followed by filling said testers with blood and sampling the readings thereof, and then immediately applying said calibration fluids to said testers and taking an additional sampling thereof, whereby said testers are calibrated both immediately before and immediately after the testing of blood such that blood test results may be discarded if before and after calibration readings differ.

2. An automated blood unit comprising:
    a blood gas tester employing an electric potential;
    a blood pH tester, said pH tester providing a different test result in dependence upon a differing electrical potential in the blood therein;
    means providing intercommunication of electrical potential between said pH tester and said gas tester;
    a source of blood; and
    operational means including pump means and valve means operable under a program of control for alternatively connecting said source of blood first to said pH tester and then to said gas tester, and for first sampling said pH tester with blood in said pH tester but not in said gas tester and then sampling said pH tester with blood in both said pH tester and said gas tester, whereby a difference between the first and second pH tests will indicate a possibility of an electrically responding failure in said gas detector.

3. The automated blood unit according to claim 2 wherein said gas tester comprises a membrane tester of the type having electrical potential applied to the non-blood side of the membranes therein, whereby a difference between the first and second pH tests will indicate a possibility of a membrane failure in said gas detector.

4. Automated blood apparatus for reducing measurement time by preconditioning at least one test site comprising:
    a blood gas tester;
    a source of blood;
    a source of washout water;
    a pressurized source of calibration gas for said blood gas tester;
    means interconnecting said calibration gas source with said washout water source for providing a determinable concentration of said calibration gas in said washout water; and
    operational means including pumps and valves operative under a program of control for first providing blood to said gas tester for testing the gas content thereof, and then providing washout water to said gas tester for washing the blood therefrom, while at the same time maintaining in said gas tester a certain concentration of said gas, and for thereafter applying calibration gas to said gas tester to enable the taking of a calibration reading therein, whereby the equilibration time required between applying the calibration gas to said gas tester and the time at which a sampling thereof can be made is reduced as a result of there being a determined concentration of said calibration gas established and maintained in said washout water.

5. Automated blood apparatus according to claim 4 wherein said calibration gas source comprises a pair of sources, one having a high concentration of said calibration gas therein and the other having a lower concentration of said calibration gas therein, said washout water being connected to said high concentration calibration gas and said gas tester being thereafter calibrated with said lower concentration calibration gas in response to operation of said operational means.

6. Automated blood apparatus comprising:
    a fluid source;
    a primary pump having a push stroke and a pull stroke;
    a first fluid means valve actuated in conjunction with said primary pump and having two positions, said valve when in one position receiving fluid from the push stroke of said pump and dumping said fluid to waste;

a blood pH tester;
a blood gas tester;
second and third fluid valve means each operated between two positions in conjunction with one another, said second valve means connecting said fluid source with said gas tester when in a first of its positions, said third valve means connecting said gas tester with said first valve means when in a first of its positions, said first and second valve means, when in their second of said positions connecting said fluid source with said pH tester and connecting said pH tester with said first valve means, said first valve means when in a second of its positions connecting said third valve means with said pump, whereby a pull stroke of said pump draws fluids through said gas tester when said second and third valves are in said first position and draws fluid through said pH tester when said second and third valves are in said second position; and
means for simultaneously operating said pump and said first valve so as to draw fluid from said source through said first valve and into said pump and thereafter to expel fluid from said pump through said first valve to waste, and for alternatively operating said second and third valves between their two positions so that fluid is alternatively drawn through said gas tester or said pH tester and discharged to waste.

7. Automated blood apparatus according to claim 6 additionally comprising:
a source of calibration gas under pressure, said second valve means connecting said gas tester with waste when in a second of its positions and said third valve means connecting said gas tester with said source of calibration fluid when in its second position, whereby said calibration gas pushes fluid to waste through said gas tester at the time that said pump means is drawing fluid through said pH tester.

8. A method of monitoring blood comprising the steps of:
introducing calibration fluids under pressure into respective parts of a blood monitoring apparatus and displacing the calibration fluids respectively to diverse blood monitoring sites of the apparatus;
calibrating each monitoring site in conjunction with the calibration fluid present at said site;
retaining the calibration fluids as disposed in the apparatus following calibration;
introducing blood into the apparatus and displacing the blood to and from one or more of the monitoring sites using at least in part the calibration fluids to cause said displacement of the blood.

9. A method of circulating fluids in a blood examination system comprising at least one blood testing site to enhance blood clean out comprising the steps of:
displacing blood obtained from a patient in a one direction to the testing site;
testing the blood at the site;
displacing the blood by reverse flow two cleaning fluids by creating a wash solution/gas interface at the testing site and alternating displacing the wash solution and gas in generally opposite direction to and away from the site to scrub the site of any residual blood whereby accurate testing of sequential blood samples is achieved at the site.

* * * * *